US 7,651,672 B2

(12) United States Patent
Lin et al.

(10) Patent No.: US 7,651,672 B2
(45) Date of Patent: *Jan. 26, 2010

(54) CABINET TYPE ENDOSCOPE PROCESSOR

(75) Inventors: Szu-Min Lin, Irvine, CA (US); Robert C. Platt, Jr., Laguna Niguel, CA (US); Vinod Mirchandani, Sam Ramon, CA (US)

(73) Assignee: Ethicon, Inc., Somerville, NJ (US)

( * ) Notice: Subject to any disclaimer, the term of this patent is extended or adjusted under 35 U.S.C. 154(b) by 118 days.

This patent is subject to a terminal disclaimer.

(21) Appl. No.: 11/321,247

(22) Filed: Dec. 29, 2005

(65) Prior Publication Data

US 2007/0154346 A1   Jul. 5, 2007

(51) Int. Cl.
*A61L 9/00* (2006.01)
*A61L 2/00* (2006.01)
*B08B 9/027* (2006.01)
*A61B 1/12* (2006.01)
*A61L 2/18* (2006.01)

(52) U.S. Cl. .................. 422/300; 422/28; 134/22.11; 600/155; 600/156

(58) Field of Classification Search ............... 422/300; 600/101, 155, 156; 134/22.11
See application file for complete search history.

(56) References Cited

U.S. PATENT DOCUMENTS

| | | | |
|---|---|---|---|
| 4,278,101 A | 7/1981 | Tanaka et al. | |
| 4,380,530 A | 4/1983 | Kaye | |
| 4,489,741 A | 12/1984 | Ogasawara | |
| 4,493,706 A * | 1/1985 | Borsanyi et al. | 604/153 |
| 4,911,190 A | 3/1990 | Sheldon | |
| 5,090,433 A | 2/1992 | Kamaga | |
| 5,288,467 A | 2/1994 | Biermaier | |

(Continued)

FOREIGN PATENT DOCUMENTS

DE   3819257 C1   7/1989

(Continued)

OTHER PUBLICATIONS

Biermaier, Hans; English Abstract of EP0345713 for equivalent patent DE 3819257, Dec. 13, 1999; 2007 Micropatent LLC.

*Primary Examiner*—Sean Conley
*Assistant Examiner*—Kevin Joyner

(57) ABSTRACT

An endoscope processor, according to the present invention, provides for cleaning and sterilizing an endoscope having a body, and a first flexible tube attached to the body. It includes an operational housing and an enclosure which is attachable to and detachable from the operational housing, the enclosure being sealed from ingress of potentially contaminating microorganisms when detached from the operational housing. The enclosure is shaped, sized and oriented to receive the endoscope in an orientation with the first flexible tube depending vertically downwardly from the endoscope body. The enclosure includes a liquid inlet and a liquid outlet. The operational housing includes a circulating system comprising at least one liquid pump having a pump outlet connected to the liquid inlet of the enclosure when the enclosure is attached to the operational housing, and a pump inlet connected to the liquid outlet of the enclosure when the enclosure is attached to the operational housing, whereby to circulate liquid through the enclosure. A source of sterilizing fluid is associated with the pump and a control system is programmed to control a sterilization procedure whereby the pump circulates a liquid comprising the sterilizing fluid through the enclosure.

21 Claims, 9 Drawing Sheets

U.S. PATENT DOCUMENTS

| | | |
|---|---|---|
| 5,405,587 A | 4/1995 | Fernandez |
| 5,425,815 A | 6/1995 | Parker et al. |
| 5,534,221 A | 7/1996 | Hillebrenner et al. |
| 5,830,127 A | 11/1998 | DeCastro |
| 5,851,485 A | 12/1998 | Lin et al. |
| 6,030,579 A | 2/2000 | Addy et al. |
| 6,041,794 A * | 3/2000 | Lin et al. ............ 134/22.11 |
| 6,068,815 A | 5/2000 | Oberleitner et al. |
| 6,555,054 B1 | 4/2003 | Kral et al. |
| 6,797,245 B2 | 9/2004 | Nakanishi et al. |
| 2004/0091389 A1* | 5/2004 | Malkin et al. ............ 422/26 |
| 2004/0118413 A1 | 6/2004 | Williams et al. |
| 2005/0025664 A1* | 2/2005 | Selig et al. ............ 422/28 |
| 2006/0269442 A1 | 11/2006 | Nguyen et al. |
| 2007/0100206 A1 | 5/2007 | Lin et al. |
| 2007/0154371 A1 | 7/2007 | Lin et al. |

FOREIGN PATENT DOCUMENTS

| | | |
|---|---|---|
| EP | 1016371 A1 | 7/2000 |
| WO | WO 01/56615 A3 | 8/2001 |
| WO | WO 0156459 A1 | 8/2001 |
| WO | WO 0156615 A2 | 8/2001 |
| WO | WO 2005056060 A1 | 6/2005 |

* cited by examiner

FIG. 1 *PRIOR ART*

CABINET TYPE ENDOSCOPE PROCESSOR

BACKGROUND OF THE INVENTION

The present invention relates to endoscope washing and decontamination.

Devices exist for washing and decontaminating endoscopes automatically. They are typically termed automated endoscope reprocessors (AER). One such device is shown in U.S. Published Patent Application No. 2004/0118413 published Jun. 24, 2004, incorporated herein by reference (the '413 application). Typical AER will comprise a basin into which the endoscope is coiled and into which flows solution for cleaning and disinfection or sterilization. Individual connections are typically made to the various connectors on the endoscope to provide fluid under pressure to those channels for washing and disinfection. At the end of the procedure the endoscope is removed from the basin. Accordingly, even if the endoscope where completely sterilized in the procedure, its removal from the basin would break that sterility.

A system has been devised in which an endoscope is coiled into a cassette, which cassette is then placed into the basin for processing. When the cassette is removed from the AER the endoscope maintains its sterility within the cassette. Please see U.S. Pat. No. 5,534,221, incorporated herein by reference. However, such a cassette is not suitable for long-term storage of most endoscopes. Due to the delicate nature of their internal structure, it can be harmful to leave them coiled for extended periods of time.

SUMMARY OF THE INVENTION

An endoscope processor, according to the present invention, provides for cleaning and sterilizing an endoscope having a body, and a first flexible tube attached to the body. The endoscope processor comprises an operational housing and an enclosure which is attachable to and detachable from the operational housing, the enclosure being sealed from ingress of potentially contaminating microorganisms when detached from the operational housing. The enclosure is shaped, sized and oriented to receive the endoscope in an orientation with the first flexible tube depending vertically downwardly from the endoscope body. The enclosure includes a liquid inlet and a liquid outlet. The operational housing comprises a circulating system comprising at least one liquid pump having a pump outlet connected to the liquid inlet of the enclosure when the enclosure is attached to the operational housing, and a pump inlet connected to the liquid outlet of the enclosure when the enclosure is attached to the operational housing, whereby to circulate liquid through the enclosure. A source of sterilizing fluid is associated with the pump and a control system is programmed to control a sterilization procedure whereby the pump circulates a liquid comprising the sterilizing fluid through the enclosure.

Preferably, the enclosure comprises a first downwardly depending space to receive the first flexible tube of the endoscope depending downwardly, and a second downwardly depending space, separated from the first downwardly depending space, to receive, depending downwardly, a second flexible tube attached to the endoscope body. Preferably, the receiving space is sized and shaped to closely fit the size and shape of the endoscope.

Preferably, the endoscope rests upon a supporting surface between the first depending space and the second depending space and movement means are provided to move the supporting surface during a sterilization procedure whereby to reduce occlusion between the supporting surface and the endoscope. Given that liquid is flowing in the enclosure, it is preferable to effect movement of the supporting surface via use of flowing liquid under pressure, as for instance to induce rotation of the supporting surface. Mechanical methods such as a motor can also be employed to effect movement.

Preferably, the endoscope processor includes a source of washing fluid so that the control system can be programmed to control a washing procedure followed by a sterilization procedure.

Preferably, the enclosure further comprises a series of connections for supplying liquid to one or more lumens in the endoscope during the process.

In one aspect of the invention, a vacuum pump is provided which is connectable to the receiving space and capable of vaporizing a sterilant therein. A sterilizing fluid comprising peracetic acid or hydrogen peroxide is useful for liquid sterilization and particularly useful when employing a vacuum pump to vaporize the sterilant and provide a sterilizing vapor.

A method for sterilizing and storing in sterile form an endoscope which comprises a body and a first flexible tube attached thereto, the method comprises the steps of: placing the endoscope into an enclosure in an orientation with the first flexible tube depending downwardly vertically from the endoscope body and sealing the enclosure from a surrounding environment; attaching the enclosure to an operational housing; circulating a liquid containing a sterilizing fluid from the operational housing through the enclosure to sterilize the endoscope; disconnecting the enclosure from the operational housing and storing the endoscope therein in sterile form until it is ready to be used again.

DETAILED DESCRIPTION OF THE DRAWINGS

Figure 1:
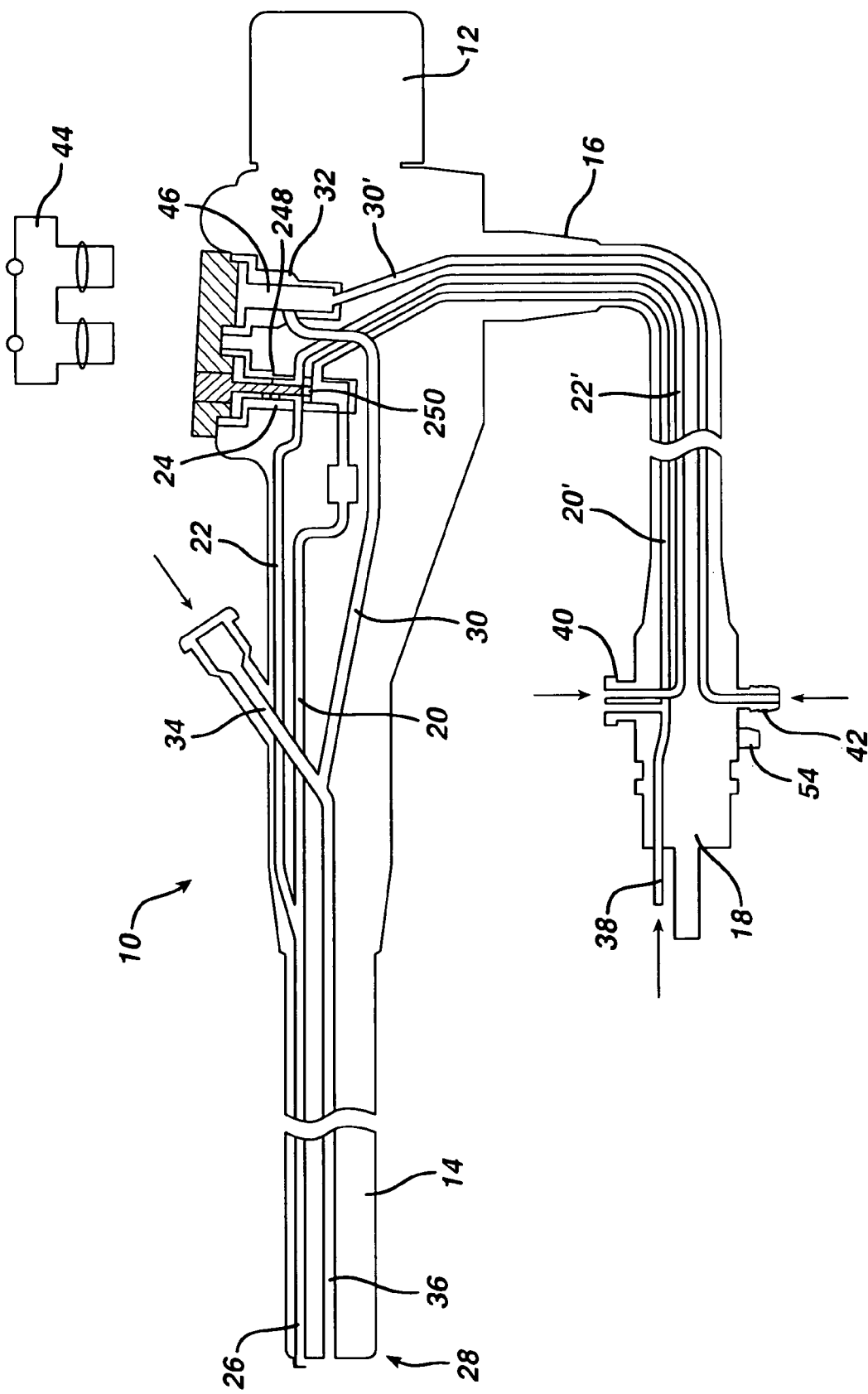
FIG. 1 is a cut-away view of an endoscope (prior art) which can be processed in the present invention.

FIG. 1 shows an endoscope 10 having a control head 12 and a flexible insertion tube 14 extending there from. An umbilical cord 16 connects the control head 12 to a light housing 18. An air channel 20 and a water channel 22 intersect a first cavity 24 in the control head 12. They extend from the first cavity 24 down the insertion tube 14 intersecting to form a combined air and water channel 26 which extends to a distal end 28 of the insertion tube. A suction channel 30 extends from a second cavity 32 in the control head 12 down the insertion tube and intersects with a biopsy or instrument channel 34 to form a combined suction/biopsy channel 36 which extends to the distal end 28.

The channels extend also from the control head 12 to the light housing 18 through the umbilical cord 16 and in that section will be given their numeral designator with the addition of a prime symbol. The air channel 20' extends from the first cavity 24 to terminate at a port 38 in the light housing 18. The water channel 22' extends from the first cavity 24 to terminate at a port 40 in the light housing 18. The suction channel 30' extends from the second cavity 32 to terminate in a port 42 in the light housing 18.

A valve mechanism 44 fits within the first and second cavities 24 and 32 to control flow of air, water and suction during operation of the endoscope 10. During cleaning and sterilization the valve mechanism is removed and placed into a cage (not shown in FIG. 1) for processing with the endoscope 10. A channel separator 46 is inserted into the first and second cavities 24 and 32 to isolate the air channel 20 from the water channel 22 and to enclose the first and second cavities 24 and 32.

Figure 2:
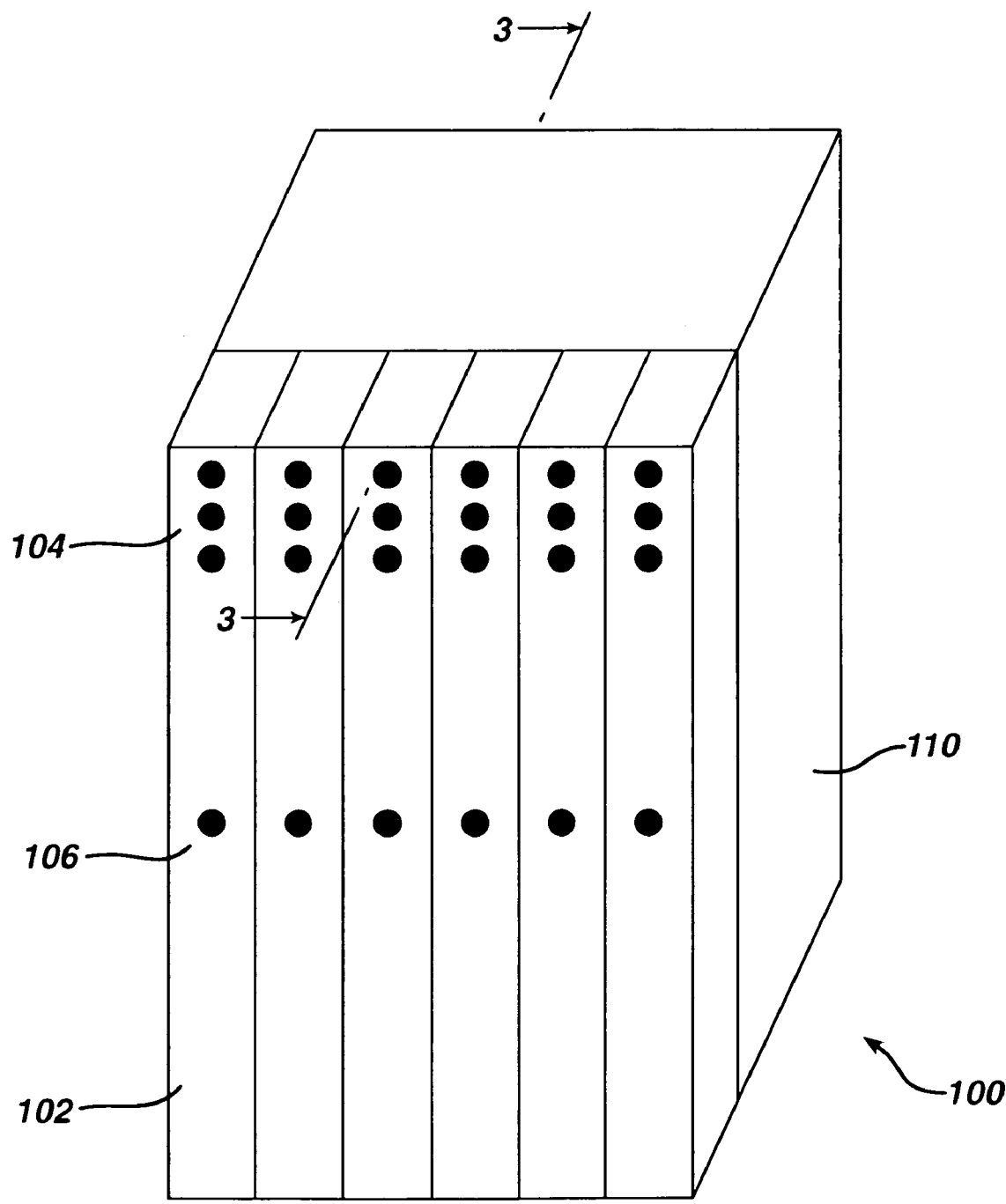
FIG. 2 is a front perspective view of an endoscope processor according to the present invention.

Turning also now to FIG. 2, an endoscope processor system 100 is shown. It comprises a plurality of independent cabinets 102, each adapted for processing an endoscope 10. Status lights 104 or other indicators are preferably provided on each cabinet 102 to show the status of whether the cabinet is loaded with an endoscope 10, and whether processing has been completed and completed successfully, as well as other information which might be useful to an operator. Handles 106 and castors 108 are provided for easy maneuvering of the cabinets 102.

Figure 3:
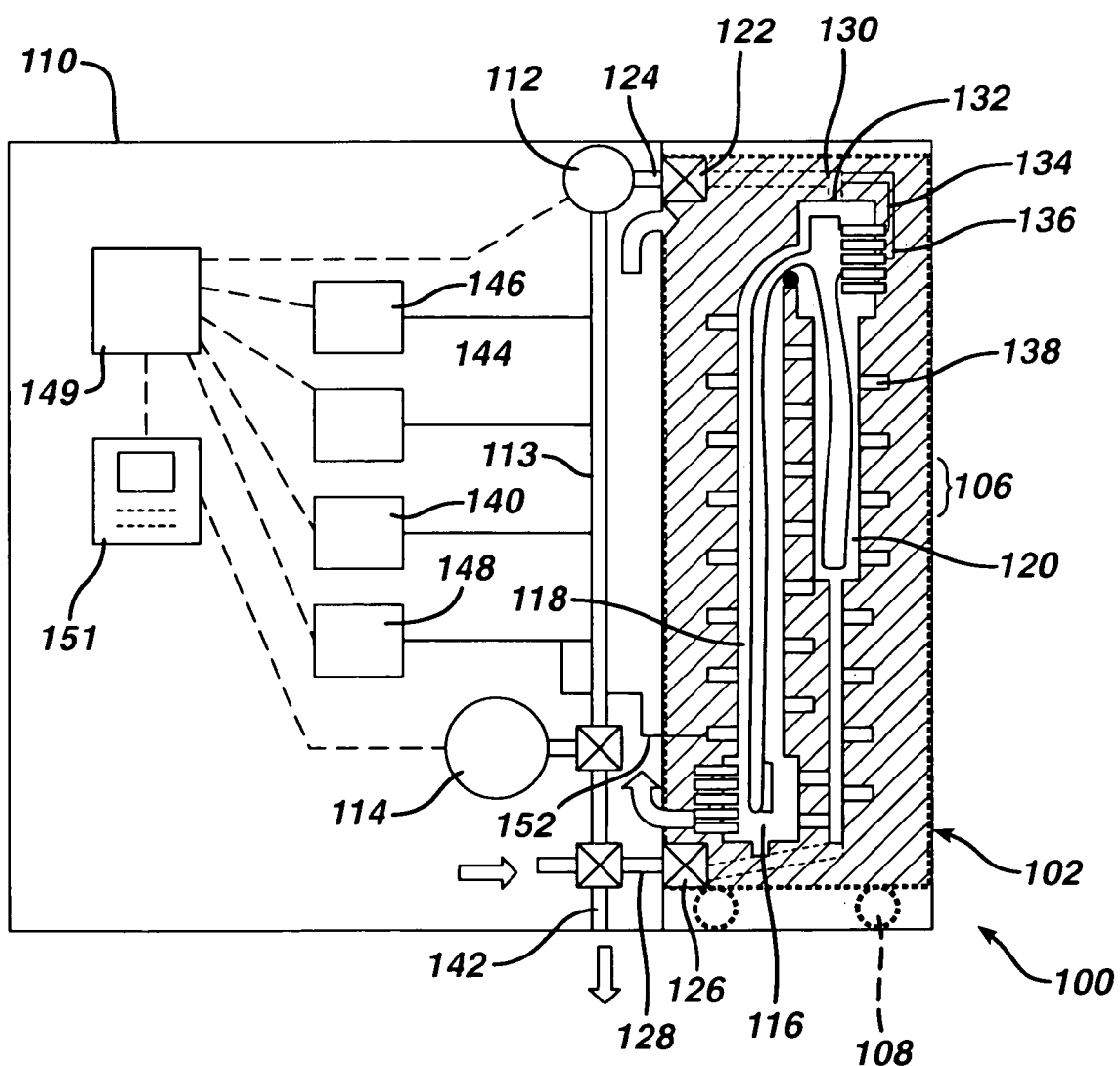
FIG. 3 is a sectional view taken along lines 3-3 of FIG. 2.

Turning also now to FIG. 3, the cabinet 102 connects to a main housing 110 which contains a fluid pump 112 and vacuum pump 114 and associated circulation plumbing 113. Interior of the cabinet 102 is an endoscope receiving space 116 having a first depending cavity 118 for receiving the endoscope umbilical cord 16 and a second depending cavity 120 for receiving the endoscope insertion tube 14. Preferably, the endoscope will fit closely within the receiving space 116. Many endoscopes have flexible tubing over a meter long so the cabinet 102 should be of sufficient height to accommodate them. A supply connection 122 on the cabinet 102 connects to an outlet connection 124 on the housing 110 and a return connection 126 on the cabinet 102 connects to an inlet connection 128 on the housing 110. Each of the supply connection 122 and return connection 126 are preferably of the self closing type such that when disconnected from the housing 110 they remain closed leaving the receiving space 116 sealed.

A supply manifold 130 leads from the supply connection to a valve 132 feeding the interior space 116 and to a valve 134 feeding a channel connector 136. The channel connector 136 supplies fluid to each of the channels in the endoscope 10 and will be described in more detail later. Alternatively, multiple connections between the cabinet 102 and the housing 110 can be made so that each channel in the endoscope 10 can be fed by an individual supply line, preferably each controlled by a constant volume pump in the control housing and drawing flow from the circulating plumbing 113. Examples of such plumbing in an endoscope reprocessor are known to those of skill in the art and include the '413 application. The supply manifold further supplies liquid to a plurality of nozzles 138 lining the receiving space 116. These nozzles 138 enhance the ability to flow liquid over the endoscope 110 and thereby enhance the cleaning action, but if sufficient flow is achieved through the first and second depending cavities 118 and 120 the nozzles 138 can be omitted.

Cleaning and sterilization of an endoscope are achieved by first flowing a cleaning liquid, including a detergent and/or other cleaning agents supplied to the flow by a detergent dispensing system 140. It flows through the channel connector 136 into each of the endoscope channels (i.e. the air channels 20 and 20', water channels 22 and 22', suction channels 30 and 30' and the biopsy channel 34), through the valve 132 into the interior space 116 and through the first and second depending cavities 118 and 120, and through the nozzles 138. It drains from the bottom of the first and second depending cavities 118 and 120 and returns to the pump 112 through the return connection 126. The system is then drained through a drain 142 and fresh filtered rinse water supplied from a water supply system 144. The rinse water flows similarly and is drained. A supply of fresh filtered water is added along with a steriliant such as orthophthalaldehye, gluteraldehyde, hydrogen peroxide or peracetic acid, from a steriliant supply system 146. After the steriliant solution has been circulated for a sufficient time to effect the desired level of disinfection or sterilization it is drained a rinse performed with fresh filtered rinse water. An alcohol rinse could follow. Preferably, clean filtered air from an air supply system 148 is blown through the system to dry the endoscope 10, its channels, and the receiving space 116. Preferably, a controller 149, having a display and input device 151, controls such a cycle. The cycle is described in general terms only; other features as may be known to those of skill in the art may be incorporated therein, such as processes for checking the integrity of connections, checking for channel blockages etc.

The vacuum pump 114 can be employed to enhance the cycle. After cleaning and exposure to a liquid sterilant which is vaporizable to produce a vapor sterilant, such as hydrogen peroxide or peracetic acid, the vacuum pump 114 can be employed to lower pressure within the receiving space 116 to vaporize the liquid sterilant thereby drying the endoscope 10 and exposing it to a sterilizing vapor. Temperature, pressure, peroxide amount and concentration, and pump down rate affect the overall efficacy. A pressure of about 5 to 10 torr and a temperature of about 30° to 45° C. are desirable. Details of such a process can be found in U.S. Pat. No. 5,851,485 and U.S. Pat. No. 6,030,579, incorporated herein by reference. Especially if pumping to lower pressures, it may be desirable to provide separate lines and connections from the vacuum pump 114 and the cabinet 102 along with the ability to close the other connections such as at 124 and 128 thereby simplifying the seals needed to maintain a vacuum in the receiving space 116.

Figure 4:
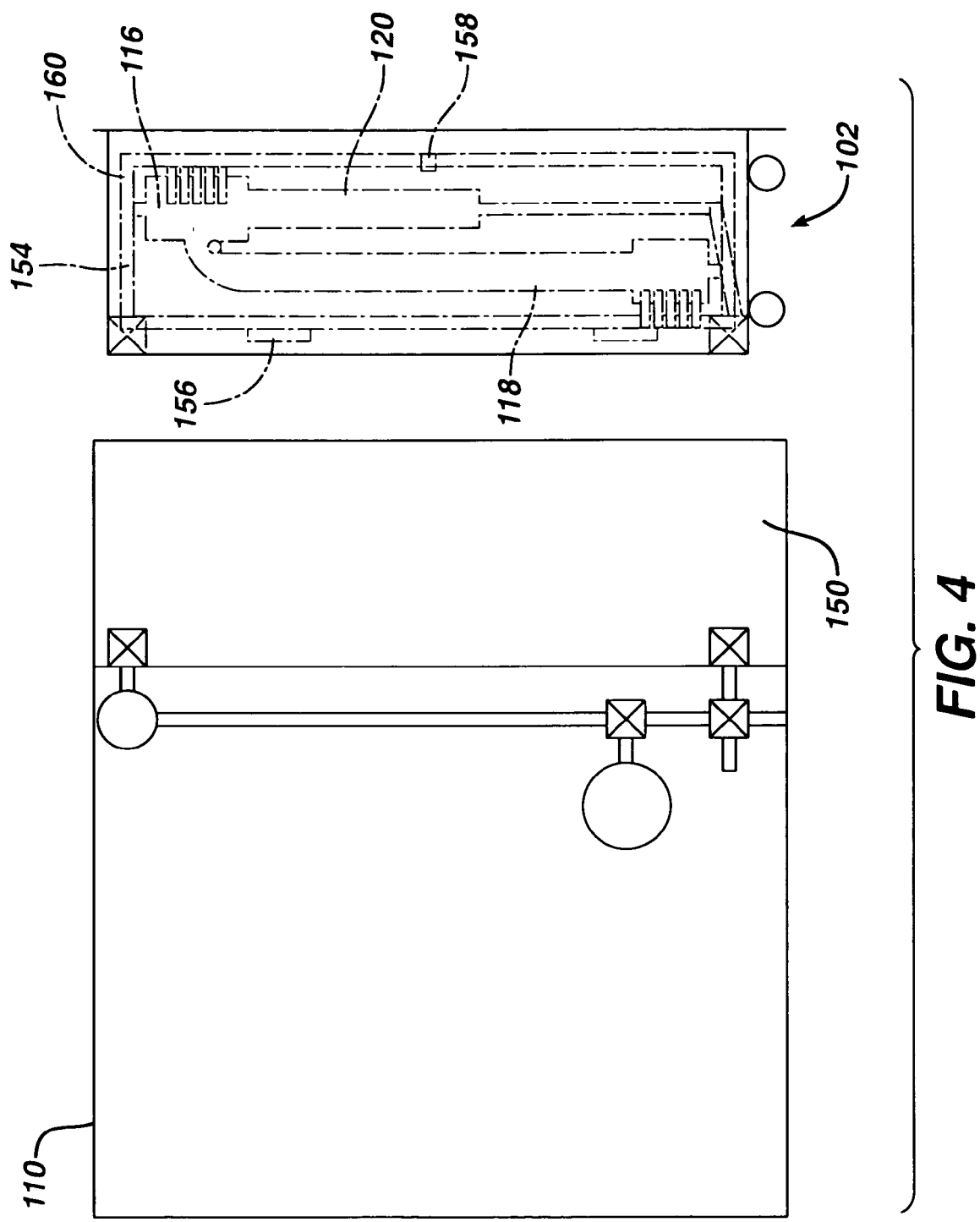
FIG. 4 is a side perspective view of the endoscope processor of FIG. 2, showing one of the cabinets moved out.

Turning also now to FIG. 4, the cabinet 102 moves on castors 108 from a position disposed exterior of an open compartment 150 (FIG. 4) to a position interior thereof (FIG. 3) wherein the supply connection 122 mates with the outlet connection 124, the return connection 126 mates with the inlet connection 128 and other electrical and fluid connections are made. Preferably the cabinet 102 contains sensors for temperature and pressure and also electrical connections to operate the valves 132 and 134 and the lights 104 as well as other electrical devices as may be desired therein. An air supply connection 152 can be provided for testing the integrity of the endoscope 10 sheath via a port 154 which leads to a space within the endoscope internal of the sheath.

The endoscope 10 can be loaded into the receiving space 116 through a side door 154 having hinges 156 and a latch 158. A seal 160 around the door 154 prevents liquids from the washing and liquid sterilant portions of the cycle from leaking out, and prevents air from infiltrating in during a vacuum portion of the cycle if such is employed. It also maintains sterility of the endoscope 10 after a sterilization process be preventing ingress of potentially contaminating microorganisms.

Figure 5:
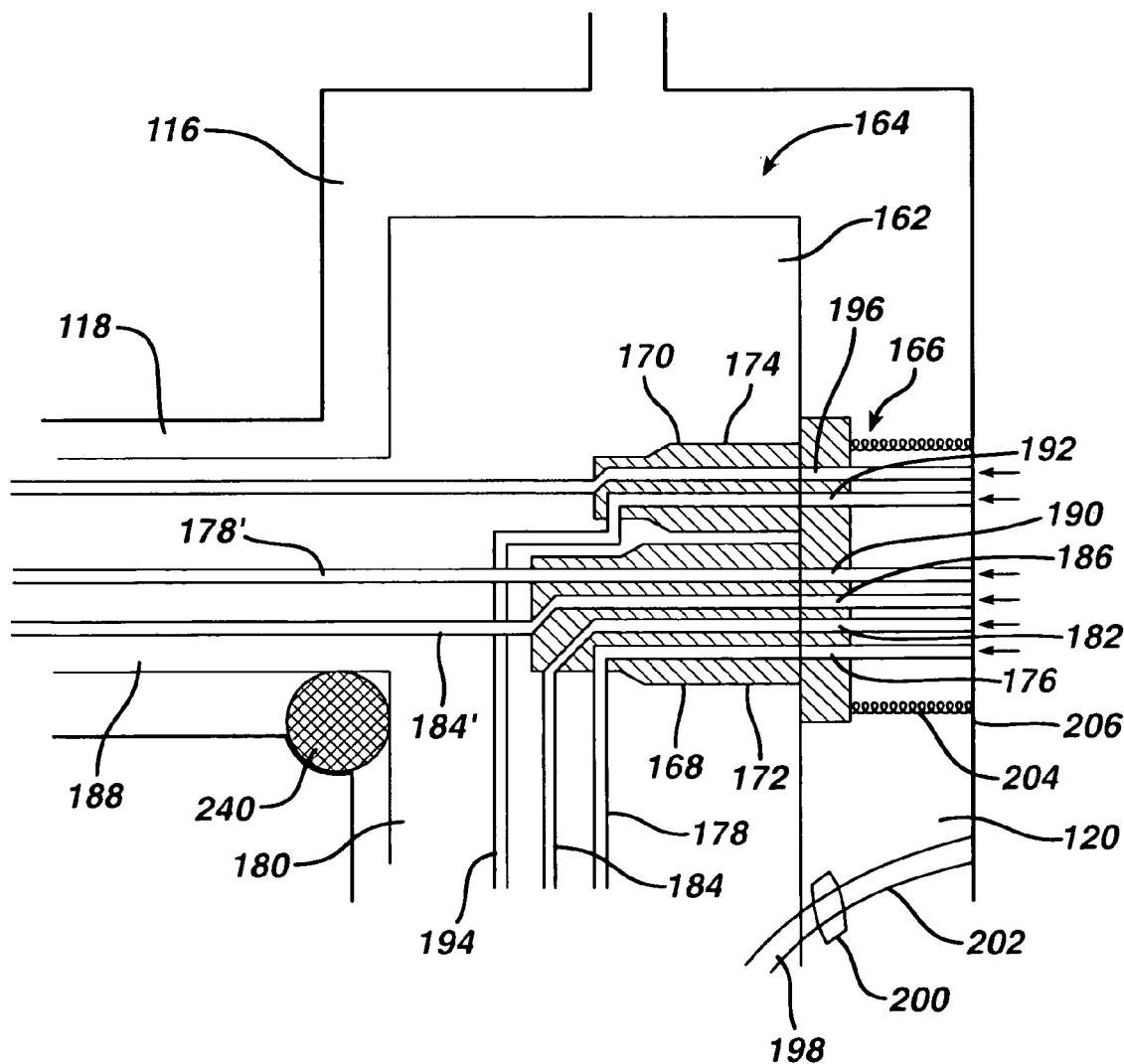
FIG. 5 is a detailed cut-away view of an endoscope within one of the cabinets of the endoscope processor of FIG. 2.

Turning also now to FIG. 5, the channel connector 136 is shown in greater detail fitted within a control head 162 of an endoscope 164. (Please note that while the structure of the endoscope 164 differs slightly from the endoscope 10 in placement of the channels it otherwise corresponds and similar terminology is used in its description. The present invention is intended for general use and each endoscope will have its own structure and channel arrangement.) It comprises a body 166 adapted to fit closely within first and second cavities 168 and 170 of the control head 162 and having a plurality of channels therethrough. A first body portion 172 fits within the first cavity 168 and a second body portion 174 fits within the second cavity 170. A first channel 176 passes through the first body portion 172 to intersect with a water channel 178 in an insertion tube 180 of the endoscope 164. A second channel 182 passes through the first body portion 172 to intersect with an air channel 184. A third channel 186 passes through the first body portion 172 to intersect with an umbilical cord 188 portion of the air channel 184' (note that the umbilical cord 184 portions of the channels are designated with a prime). A fourth channel 190 passes through the first body portion 172 to intersect with the water channel 178'. A fifth channel 192 passes through the second body portion 174 to intersect with a suction channel 194 and a sixth channel 196 passes through the second body portion 174 to intersect with the suction channel 194'.

Each of the first through sixth channels 176, 182, 186, 190, 192 and 196 connect either directly or through intermediate tubing to the supply manifold 130 downstream of the valve 134. Preferably, rather than a single supply manifold 130 individual lines and connections are provided on the cabinet 102 connecting to individual pumps in the housing 110 for each of these channels in the channel connector 136. Also, in addition to these connections, most endoscopes have a separate biopsy channel 198 and associated connector 200 an additional connection, such as with a connection tubing 202 as is known in the art. A non-occluding connection such as taught in pending U.S. patent application Ser. No. 11/141, 431, incorporated herein by reference, in which the connector has flaps which move away from the connection surface under certain flow conditions, such as high flow, to limit occlusions are preferred.

Reduction of occlusions during the process is to be desired. If the channel connector 136 were to be moved inwardly and outwardly at points during the cycle, the areas in which it contacts the first and second cavities 168 and 170 would be contacted with cleaning and sterilization fluid. Mechanical means can be provided to impart such movement, such as a motor and linkage connected thereto. However, it is preferred to limit the complexity as there is a desire to keep the cost of the cabinet 102 to a minimum as it is employed for storage as well as for cleaning and sterilization and a typical user might desire a separate cabinet for each of their endoscopes.

To economize the function of reducing occlusion via channel connector 136 movement it is desirable to employ the energy contained within the flowing fluids to effect such movement, thereby negating the requirement for additional expensive equipment. Springs 204 between a surface 206 forming a portion of the receiving space 116 and the channel connector 136 urge the channel connector 136 inwardly of the first and second cavities 168 and 170. Extra flow through its channels provides pressure tending to urge the channel connector 136 outwardly. Thus, by controlling flow through the channels the position of the channel connector can be changed.

Figure 6:
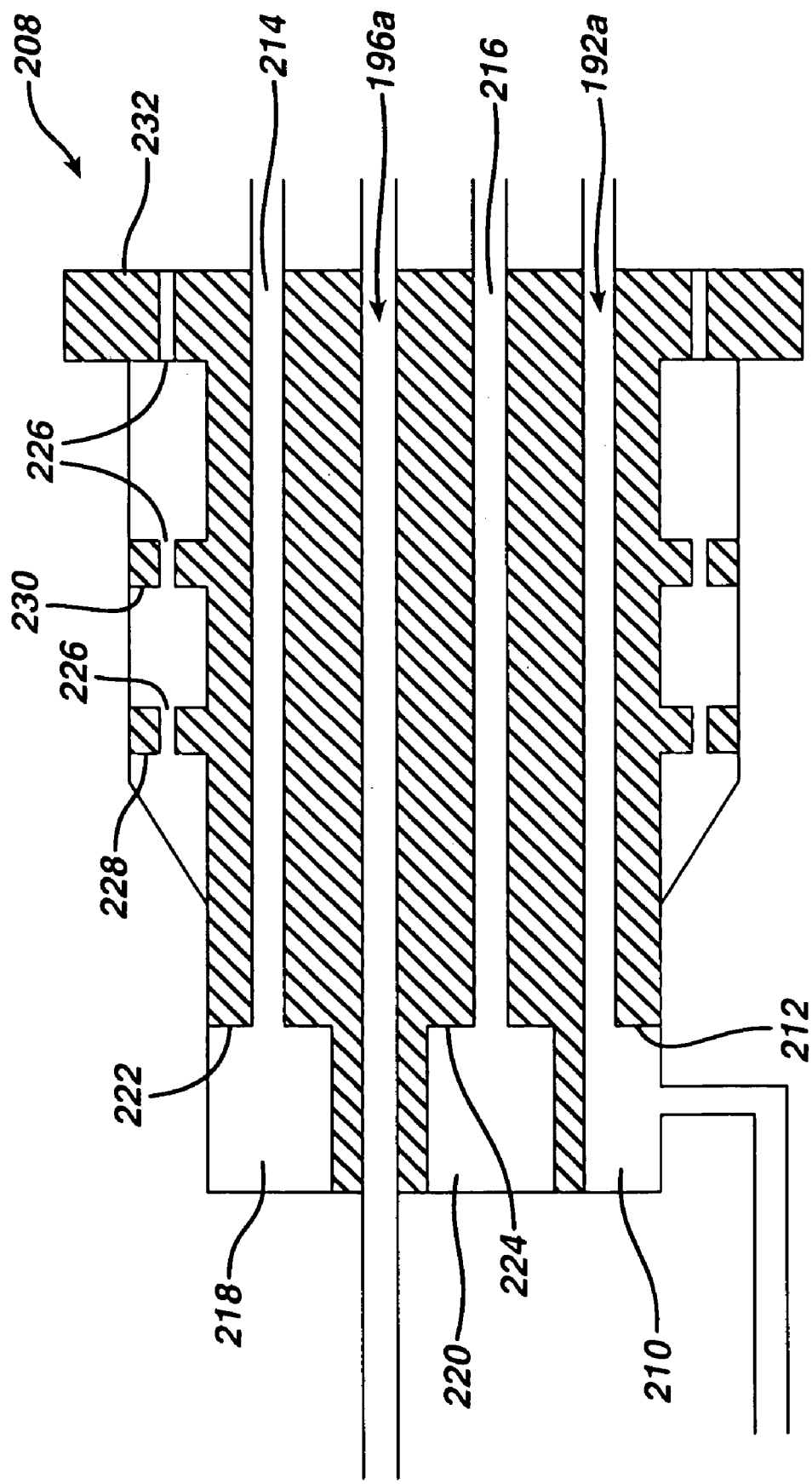
FIG. 6 is a cut-away view of a portion of a channel connector for use in the endoscope processor of FIG. 2.

The structure of the channel connector 136 can enhance this ability. Turning also to FIG. 6, which shows a first embodiment 208 of the second body portion 174a (it is the lesser in complexity) of the channel connector 136. Parts herein which are generic and described before, will be designated with a following character "a." The fifth channel 192a terminates in a space 210 having a surface 212 whereupon flow therethrough increases pressure on the surface 212 to urge the second body portion 174a outwardly of the second cavity 170. Separate channels 214 and 216 terminate in spaces 218 and 220 with surfaces 222 and 224 whereupon flow into the spaces 218 and 220 would tend to urge the second body portion 174a outwardly. Openings 226 through annular positioning flanges 228, 230 and an outer body portion 232 allow outward movement without a suction blockage.

Figure 7:
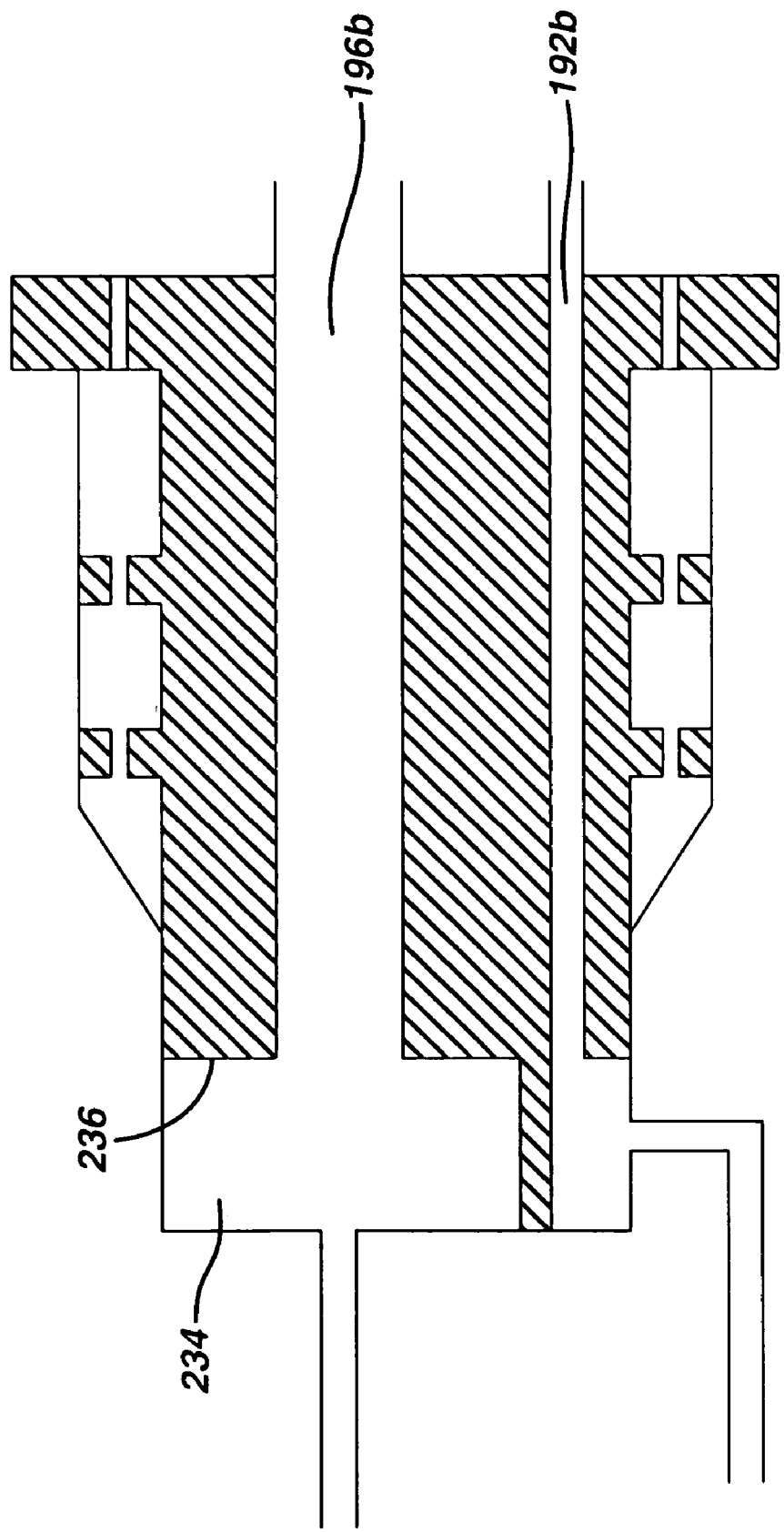
FIG. 7 is a cut-away view of an alternative channel connector.

Turning also to FIG. 7, an alternative approach, with sublabels "b" employs rather than separate channels 214 and 216, a channel 196b which opens into a space 234 with a surface 236 which allows flow therethrough to create a pressure which urges the second body portion 174b outwardly. A regular washing flow is not sufficient to overcome the force of the springs 204, whereas an increased flow creates a pressure sufficient to overcome the force of the springs 204 and move the body portion 174b outwardly.

Figure 8:
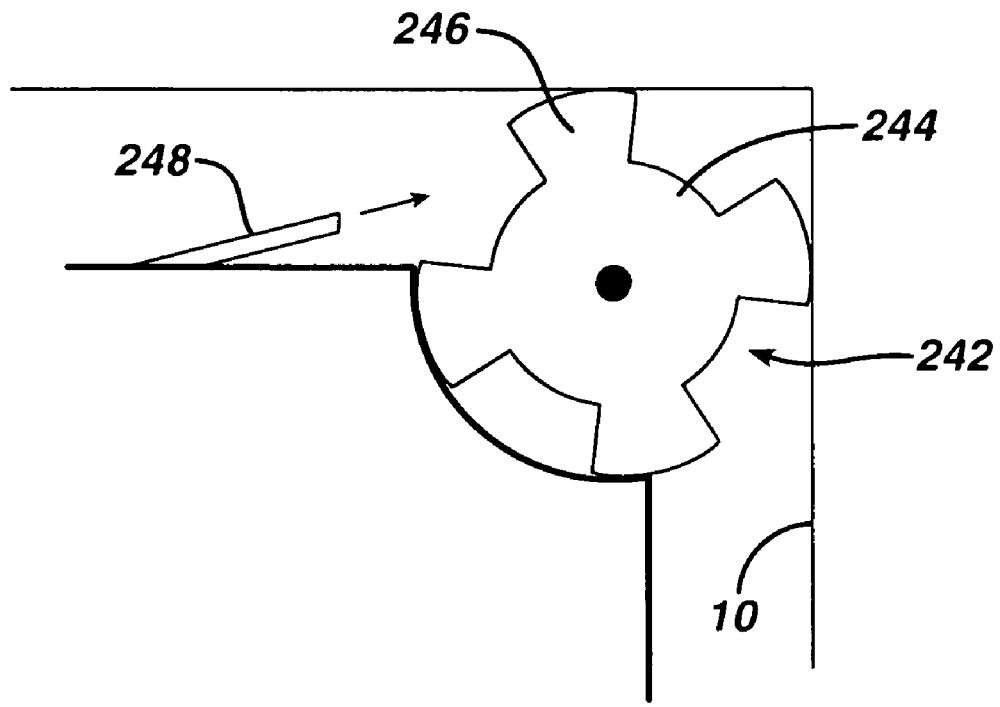
FIG. 8 is a cut-away view of a supporting surface within one of the cabinets of the endoscope processor of FIG. 2.

Turning also to FIG. 8, another source of occlusion occurs between the endoscope 10 and a contact surface 240 (FIG. 3) between the first depending cavity 118 and second depending cavity 120. In other locations the movement of the fluid therethrough should prevent continuous occlusion, but this location bears the weight of the endoscope 10 and despite fluid flow thereby the endoscope 10 may not move with respect to this contact surface 240.

Figure 8A:
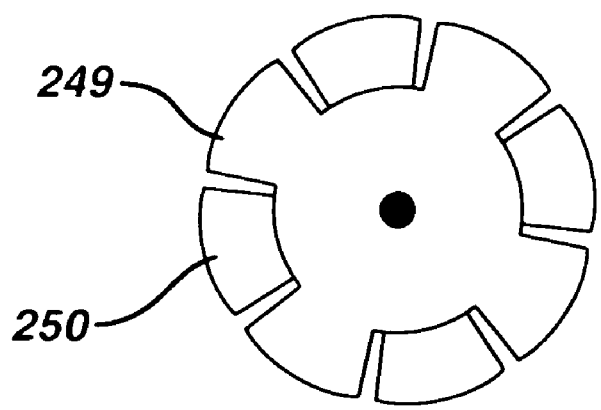
FIG. 8a is a cut-away view of an alternative supporting surface.

To alleviate issue with such occlusion, means such as a rotating contact surface 242 can be employed. The rotating contact surface 242 comprises a wheel 244 having blades 246 thereon which is urged into rotation via a jet 248 connected to the supply manifold 130 and aimed at the blades 246. A plurality of axially aligned wheels 249 and 250 rotating, preferably in opposite directions, (FIG. 8a) can also be employed so as to limit the movement of the endoscope 10 engendered by the wheels 249 and 250. Motors or other means could also be employed rather than the jet(s) 248 to effect such movement.

Figure 9:
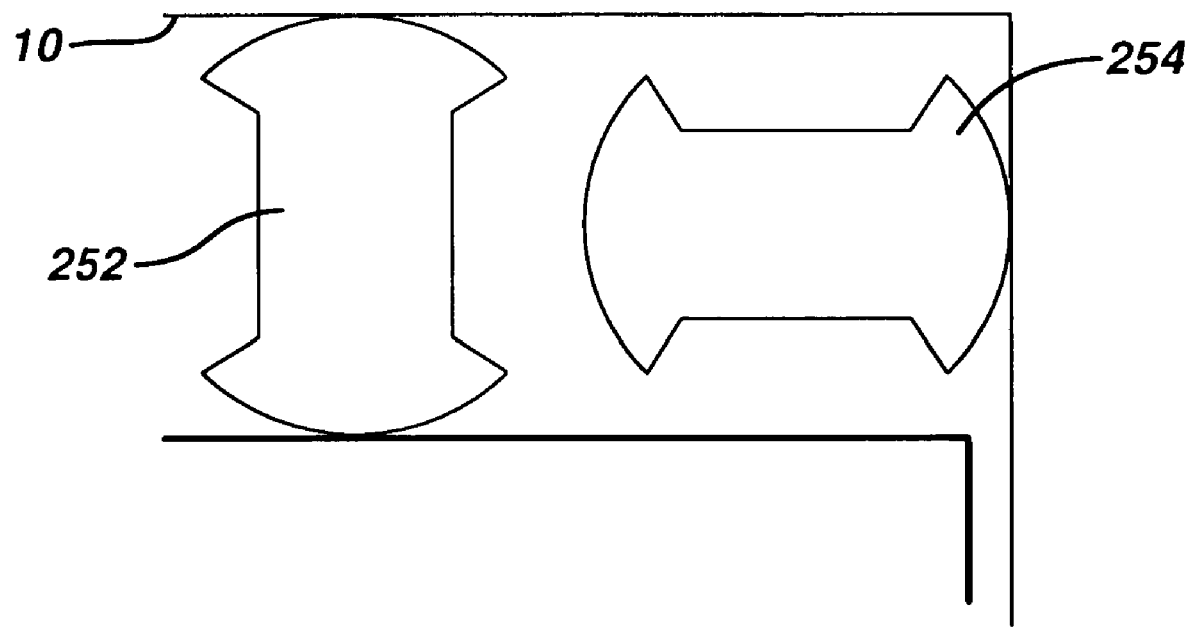
FIG. 9 is a cut-away view of a further alternative supporting surface.

Turning also to FIG. 9, first and second rotating cams 252 and 254 move the endoscope upwards and outwards respectively. They would preferably be motor driven. In addition to reducing occlusion, they would also be able to move the endoscope 10 with respect to the channel connector 136 if it were rigidly attached to the cabinet 102.

Additional disclosure on channel connectors can be found in U.S. application Ser. No. 11/263,010, incorporated herein by reference.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

What is claimed is:

1. An endoscope processor for cleaning and sterilizing an endoscope having a body, and a first flexible tube attached to the body, the endoscope processor comprising:

an operational housing;

an enclosure which is attachable to and detachable from the operational housing, the enclosure being sealed from ingress of potentially contaminating microorganisms when detached from the operational housing, the enclosure comprising:
   a first cavity configured to receive the body of the endoscope;
   a second cavity at least partially separated from the first cavity, wherein the second cavity is configured to receive the first flexible tube of the endoscope in an uncoiled configuration;
   a support surface positioned at least partially intermediate the first cavity and the second cavity, wherein a portion of the endoscope is configured to be positioned on the support surface such that the endoscope is in a hanging orientation within the enclosure at least when he enclosure is attached to the operational housing; and
   movement means configured to intermittently permit a sterilant fluid to flow between the portion of the endoscope and the support surface to reduce occlusions between the portion of the endoscope and the support surface; and
the operational housing comprising:
   a circulating system comprising at least one liquid pump having a pump outlet connected to a liquid inlet of the enclosure when the enclosure is attached to the operational housing, and a pump inlet connected to a liquid outlet of the enclosure when the enclosure is attached to the operational housing, whereby to circulate liquid through the enclosure;
   a source of sterilizing fluid associated with the pump; and
   a control system programmed to control a sterilization procedure whereby the pump circulates a liquid comprising the sterilizing fluid through the enclosure.

2. The endoscope processor according to claim 1 wherein the first and second cavities depend downwardly from the support surface at least when the enclosure is attached to the operational housing.

3. The endoscope processor according to claim 1 wherein the first and second cavities are sized and shaped to closely fit the size and shape of the endoscope.

4. The endoscope processor according to claim 1 wherein flowing liquid under pressure is employed by the movement means to effect movement of the support surface.

5. The endoscope processor according to claim 1 wherein the support surface is configured to rotate.

6. The endoscope processor according to claim 1 further comprising a source of washing fluid, wherein the control system is programmed to control a washing procedure followed by a sterilization procedure.

7. The endoscope processor according to claim 1 wherein the enclosure further comprises a series of connections for supplying the liquid to one or more lumens in the endoscope.

8. The endoscope processor according to claim 1 further comprising a vacuum pump connectable to the enclosure and capable of vaporizing a sterilant therein.

9. The endoscope processor according to claim 1 wherein the sterilizing fluid comprises peracetic acid or hydrogen peroxide.

10. An endoscope processor for cleaning and sterilizing an endoscope, wherein the endoscope includes a body and a flexible tube attached to the body, the endoscope processor comprising:
   an operational housing;
   an enclosure configured to receive the endoscope, wherein the enclosure is configured to be attached to and detached from the operational housing, and wherein the enclosure is sealed from ingress of potentially contaminating microorganisms when detached from the operational housing, the enclosure comprising:
      a cavity configured to receive the flexible tube in an uncoiled configuration; and
      a movable support surface, wherein a portion of the endoscope is configured to be positioned on the movable support surface at least when the enclosure is attached to the operational housing, and wherein the movable support surface is configured to intermittently permit a sterilant fluid to flow between the portion of the endoscope and the movable support surface to reduce occlusions between the portion of the endoscope and the movable support surface; and
   the operational housing comprising a circulating system, wherein the circulating system is configured to circulate the sterilant fluid within the enclosure when the enclosure is attached to the operational housing.

11. The endoscope processor according to claim 10 further comprising a pump and a source of the sterilant fluid, wherein the pump is configured to be in fluid communication with the source of the sterilant fluid.

12. The endoscope processor according to claim 10 further comprising a control system, wherein the control system is configured to control a sterilization procedure within the enclosure.

13. The endoscope processor according to claim 10 further comprising a rotatable member, wherein the movable support surface includes the rotatable member.

14. The endoscope processor according to claim 13 wherein the rotatable member includes at least one projection extending therefrom, wherein the projection is configured to be engaged with and disengaged from the portion of the endoscope positioned on the movable support surface to intermittently permit the sterilant fluid to flow between the portion of the endoscope and the movable support surface.

15. The endoscope processor according to claim 10 wherein the movable support surface includes a rotatable cam having at least one camming surface, and wherein the camming surface is configured to be engaged with and disengaged from the portion of the endoscope positioned on the movable support surface to intermittently permit the sterilant fluid to flow between the portion of the endoscope and the movable support surface.

16. An endoscope processor for cleaning and sterilizing an endoscope, wherein the endoscope includes a body and a flexible tube attached to the body, the endoscope processor comprising:
   an operational housing;
   an enclosure configured to receive the endoscope, wherein the enclosure is configured to be placed in and removed from fluid communication with the operational housing, and wherein the enclosure is sealed from ingress of potentially contaminating microorganisms when removed from fluid communication with the operational housing, the enclosure comprising:
      a cavity configured to receive the flexible tube of the endoscope in an uncoiled configuration;
      a side wall; and
      a biasing member configured to act against the side wall and a portion of the endoscope to intermittently permit a sterilant fluid to flow between the portion of the endoscope and the side wall to reduce occlusions between the portion of the endoscope and the side wall; and
   a circulating system, wherein the circulating system is configured to circulate the sterilant fluid within the enclosure when the enclosure is in fluid communication with the operational housing.

17. The endoscope processor according to claim 16 wherein the biasing member includes a spring.

18. The endoscope processor according to claim 16 wherein the endoscope further comprises a second portion, wherein the endoscope processor further comprises a movable support surface, wherein the second portion of the endoscope is configured to be positioned on the movable support surface when the enclosure is in fluid communication with the operational housing, and wherein the movable support surface is configured to intermittently permit the sterilant fluid to flow between the second portion of the endoscope and the movable support surface to reduce occlusions between the second portion of the endoscope and the movable support surface.

19. The endoscope processor according to claim 18 wherein the movable support surface includes a rotatable cam having at least one camming surface, and wherein the camming surface is configured to be engaged with and disengaged from the second portion of the endoscope positioned on the movable support surface to intermittently permit the sterilant fluid to flow between the second portion of the endoscope and the movable support surface.

20. The endoscope processor according to claim 18 wherein the movable support surface includes a rotatable member.

21. The endoscope processor according to claim 20 wherein the rotatable member includes at least one projection extending therefrom, wherein the projection is configured to be engaged with and disengaged from the second portion of the endoscope positioned on the movable support surface to intermittently permit the sterilant fluid to flow between the second portion of endoscope and the movable support surface.

* * * * *